US008747976B2

(12) United States Patent
Montes De Oca Balderas et al.

(10) Patent No.: US 8,747,976 B2
(45) Date of Patent: Jun. 10, 2014

(54) ORIENTATED POLYMERIC DEVICES

(75) Inventors: Horacio Montes De Oca Balderas, York (GB); Malcolm Brown, Otley (GB); Mark Bonner, Leeds (GB); Ian Macmillan Ward, Leeds (GB); Michael Andrew Hall, Middlesbrough (GB); John Rose, Collierville, TN (US); Mason James Bettenga, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 1175 days.

(21) Appl. No.: 12/596,623

(22) PCT Filed: Apr. 18, 2008

(86) PCT No.: PCT/US2008/060821
§ 371 (c)(1),
(2), (4) Date: Jun. 22, 2010

(87) PCT Pub. No.: WO2008/131221
PCT Pub. Date: Oct. 30, 2008

(65) Prior Publication Data
US 2010/0280559 A1 Nov. 4, 2010

Related U.S. Application Data

(60) Provisional application No. 60/912,740, filed on Apr. 19, 2007, provisional application No. 60/971,370, filed on Sep. 11, 2007.

(51) Int. Cl.
*B29C 47/00* (2006.01)

(52) U.S. Cl.
USPC .......................................................... 428/36.9

(58) Field of Classification Search
USPC .......................................................... 428/36.9
See application file for complete search history.

(56) References Cited

U.S. PATENT DOCUMENTS

| 3,856,905 A | 12/1974 | Dawson |
| 3,926,459 A | 12/1975 | Pontigny |
| 4,946,470 A * | 8/1990 | Sulc et al. .................... 623/6.58 |
| 4,950,258 A | 8/1990 | Kawai et al. |
| 5,108,289 A | 4/1992 | Fukuyo |

(Continued)

FOREIGN PATENT DOCUMENTS

| CN | 1569261 A | 1/2005 |
| DE | 1604403 B1 | 11/1970 |

(Continued)

OTHER PUBLICATIONS

International Search Report mailed Aug. 7, 2009, which was received in parent application No. PCT/US2008/060821, 11 pages.

(Continued)

*Primary Examiner* — James Yager
(74) *Attorney, Agent, or Firm* — Krieg DeVault LLP

(57) ABSTRACT

The present disclosure relates to a shape memory polymer material containing at least one two dimensional region having a first amount of stored stress in a first direction and a second amount of stored stress higher than the first amount of stored stress in a second direction, wherein the two dimensional region is capable of changing shape in only one of the first or second directions.

16 Claims, 6 Drawing Sheets

(56) References Cited

U.S. PATENT DOCUMENTS

| | | | |
|---|---|---|---|
| 5,951,288 | A | 9/1999 | Sawa |
| 6,160,084 | A | 12/2000 | Langer et al. |
| 6,277,390 | B1 | 8/2001 | Schaffner |
| 6,281,262 | B1* | 8/2001 | Shikinami .................... 523/105 |
| 6,299,448 | B1 | 10/2001 | Zdrahala et al. |
| 2004/0030341 | A1 | 2/2004 | Aeschlimann et al. |
| 2004/0210316 | A1* | 10/2004 | King et al. ................ 623/18.11 |
| 2005/0202194 | A1* | 9/2005 | Browne et al. .............. 428/36.9 |
| 2007/0083205 | A1 | 4/2007 | Attawia et al. |
| 2009/0149856 | A1 | 6/2009 | Paakinaho et al. |

FOREIGN PATENT DOCUMENTS

| | | |
|---|---|---|
| DE | 3036611 A1 | 6/1982 |
| DE | 102005032005 A1 | 1/2007 |
| EP | 1000958 A1 | 5/2000 |
| FR | 2863478 A1 | 6/2005 |
| GB | 1416575 A | 12/1975 |
| JP | 09234241 A | 9/1997 |
| WO | 9622061 A1 | 7/1996 |
| WO | WO 2005/013839 A2 | 2/2005 |
| WO | 2008131197 A1 | 10/2008 |

OTHER PUBLICATIONS

English Computer Translation for JP 09-234241 "Orthosis Having Thermally Deforming Property" Shimadzu Corp., 1 page.

Nulend, et al., "Increased Calcification of Growth Plate Cartilage as a Result of Compressive Force in Vitro," Arthritis & Rheumatism, 29(8):1002-1009(1986), 13 pages.

Nulend, et al., "Inhibition of Osteoclastic Bone Resorption by Mechanical Stimulation in Vitro," Arthritis & Rheumatism, 33(1):66-72 (1999), 11 pages.

International Preliminary Report on Patentability mailed Oct. 20, 2009, which was received in corresponding application No. PCT/US2008/060821, 9 pages.

English Patent Abstract of DE 102005032005 from esp@cenet, Publication Date Jan. 11, 2007.

Shen, et al., "Irradiation of Chemically Crosslinked Ultrahigh Molecular Weight Polyethylene," Journal of Polymer Science: Part B: Polymer Physics, vol. 34, 1063-1077 (1996), 15 pages.

Narkis, et al., "Some Properties of Silane-Grafted Moisture-Crosslinked Polyethylene," Polymer Engineering and Science, Sep. 1985, vol. 25, No. 13, 6 pages.

Gugumus, "Possibilities and limits of synergism with light stabilizers in polyolefins 2. UV absorbers in polyolefins," Polymer Degradation and Stability 75 (2002) 309-320, 12 pages.

Costa, et al., "Mechanisms of Crosslinking, Oxidative Degradation and Stabilization of UHMWPE," UHMWPE Biomaterials Handbook, Chapter 21, Copyright 2009, 15 pages.

Al-Malaika, et al., "Processing Effects on Antioxidant Transformation and Solutions to the Problem of Antioxidant Migration," Advances in Chemistry, American Chemical Society: Washington, DC, May 5, 1996, 15 pages.

English Patent Abstract of FR 2863478 from esp@cenet, published Jun. 17, 2005, 1 page.

Decision on Rejection; Chinese Patent Office; Chinese Patent Application No. 200880020533.9; Feb. 17, 2013; 14 pages.

Patent Examination Report; Australian Patent Office; Australian Patent Application No. 2008242761; Aug. 21, 2013; 4 pages.

* cited by examiner

ORIENTATED POLYMERIC DEVICES

CROSS-REFERENCE TO RELATED APPLICATIONS

This application is a U.S. National Phase filing of International Application No. PCT/US2008/060821 which claims priority to U.S. Patent Application No. 60/912,740 filed on Apr. 19, 2007 and U.S. Patent Application No. 60/971,370 filed on Sep. 11, 2007, the disclosures of which are incorporated herein by reference in their entirety.

BACKGROUND OF THE INVENTION

1. Field of the Invention

The present disclosure relates generally to shape memory polymers and, more particularly, shape memory polymer material for use in fixating medical devices to bone.

2. Related Art

Sleeves of shape memory polymer material may be used in fixating medical devices to bone. These sleeves include a central through hole and are placed on a medical device, such as an internal fixation device. After the sleeve is placed on the device, the device is inserted into a bone and energy is then provided to the sleeve causing the sleeve to shrink axially and expand radially. This radial expansion and axial shrinkage of the sleeve allows the sleeve to engage both the device and the inner wall of the bone, thereby fixating the device to the bone.

However, it has been noticed, especially when the energy provided to the sleeve is in the form of a heat source that is placed within the through hole of the sleeve, that the through hole expands, or relaxes away from heat source and the device. This may result in inefficient heating of the sleeve, and thereby incomplete or uneven expansion of the sleeve, and device failure due to insufficient fixation of the device to the bone.

SUMMARY OF THE INVENTION

Further features, aspects, and advantages of the present disclosure, as well as the structure and operation of various embodiments of the present disclosure, are described in detail below with reference to the accompanying drawings.

In one aspect, the present disclosure relates to a shape memory polymer material containing at least one two dimensional region having a first amount of stored stress in a first direction and a second amount of stored stress higher than the first amount of stored stress in a second direction, wherein the two dimensional region is capable of changing shape in only one of the first or second directions.

In an embodiment, the material includes the shape of a cannulated cylinder in which the two dimensional region has a shape of a contour of the cylinder. In another embodiment, the two dimensional region includes the inner surface of the cylinder. In yet another embodiment, the two dimensional region is an outer surface of the cylinder. In a further embodiment, the two dimensional region is contained between an inner and an outer surface of the cylinder. In yet a further embodiment, the material includes a shape of a cannulated rectangle or square. In an embodiment, the first direction and the second direction are perpendicular to each other.

In another embodiment, the polymer material is resorbable. In yet another embodiment, the polymer material is non-resorbable. In a further embodiment, the material includes a filler selected from a group consisting essentially of hydroxyapatite, calcium carbonate, and tricalcium phosphate. In yet a further embodiment, the material includes a porogen selected from a group consisting essentially of sodium chloride, lithium bromide, lithium iodide, calcium chloride, sodium iodide, magnesium sulphate, and calcium sulphate.

In an embodiment, the polymer material includes a polyester selected from a group including P(L)LA, poly (D) lactic acid (P(D)LA), poly (DL) lactic acid (P(DL)LA), poly(L-co-DL) lactic acid (P(LDL)LA), poly (L) lactic acid-co-glycolide (P(L)LGA)), poly (DL) lactic acid-co-glycolide (P(DL)LGA)), poly (D) lactic acid-co-glycolide (P(D)LGA)), polycaprolactone (PCL), PGA, and combinations thereof. In another embodiment, the material includes a polyacrylate. In yet another embodiment, the material includes a polymethyl methacrylate polymer or copolymer thereof. In a further embodiment, the material includes a polybutyl methacrylate polymer or copolymer thereof. In yet a further embodiment, the material includes a polybutyl methacrylate-co-polymethyl methacrylate copolymer. In an embodiment, the material includes a polystyrene copolymer.

In another aspect, the present disclosure relates to a rod having a first amount of stored radial stress located on an inner surface region of the rod and a second amount of stored radial stress higher than the first amount located on an outer surface region of the rod. In an embodiment, the outer surface expands radially and the inner surface remains unchanged upon providing energy to the rod.

In yet another aspect, the present disclosure relates to a cannulated rod having a shape memory polymer material wherein the rod includes a first amount of stored radial stress located on an inner surface region of the rod and a second amount of stored radial stress higher than the first amount located on an outer surface region of the rod. In an embodiment, the outer surface expands radially and the inner surface contracts radially upon providing energy to the rod.

In a further aspect, the present disclosure relates to a method of fixating an internal fixation device to bone. The method includes providing an internal fixation device having a sleeve of shape memory polymer material coupled to the device; inserting the internal fixation device into the bone; and providing energy to the sleeve of shape memory polymer material, wherein an outer diameter of the sleeve increases to engage an inner wall of the bone and an inner diameter of the sleeve decreases to engage the fixation device.

In yet a further aspect, the present disclosure relates to a method of fixating an internal fixation device to bone. The method includes providing an internal fixation device having a sleeve of shape memory polymer material coupled to the device; inserting the internal fixation device into the bone; and providing energy to the sleeve of shape memory polymer material, wherein an outer diameter of the sleeve increases to engage an inner wall of the bone and an inner diameter of the sleeve remains unchanged.

In an aspect, the present disclosure relates to a method of deforming a sleeve of shape memory polymer material. The method includes providing a sleeve of shape memory polymer material having an outer diameter and an inner diameter; and providing energy to the sleeve to deform the sleeve, wherein the outer diameter of the sleeve increases and the inner diameter of the sleeve decreases or remains unchanged.

In another aspect, the present disclosure relates to an internal fixation device including an interface portion; and a sleeve of shape memory polymer material coupled to the interface portion.

In a further aspect, the present disclosure relates to a shape memory polymer material having a tailored stress pattern that allows the material to expand and contract simultaneously.

BRIEF DESCRIPTION OF THE DRAWINGS

The accompanying drawings, which are incorporated in and form a part of the specification, illustrate the embodiments of the present disclosure and together with the description, serves to explain the principles of the disclosure. In the drawing.

DETAILED DESCRIPTION OF THE EMBODIMENTS

The following description of the preferred embodiment(s) is merely exemplary in nature and is in no way intended to limit the disclosure, its application, or uses.

The present disclosure relates to sleeves of shape memory polymer material having tailored expansion properties that are designed to improve the functional performance of the sleeve. Upon providing the sleeve with energy, the sleeve deforms in a pre-programmed manner such that it enhances contact with surfaces surrounding the sleeve, such as the surface of the device and/or the inner surface of the bone. These sleeves and the process for making them are provided in the following examples.

EXAMPLE ONE

A first billet including a composite of poly(D-lactic acid-co-glycolic acid) (PDLAGA) and 35% calcium carbonate (CaCO3) was produced by compression molding. The billet was 20 mm in diameter and 150 mm in length. A drill was used to create a hole, approximately 6 mm in diameter and 70 mm in length, in one end of the billet, and the other end of the billet was prepared for die drawing. A stainless steel rod, about 6 mm in diameter and 200 mm in length, was inserted into the billet and the entire billet-rod assembly was drawn through a 12 mm die at 75° C. and at 1 mm per minute. After drawing, the billet was cut into sections, approximately 30 mm long, with a hand hacksaw. The metal rod was subsequently removed from each section using a 4 mm steel rod and a 4 oz ball hammer.

A second billet, including the same dimensions and composite, was also produced by compression molding. The billet was die drawn through a 10 mm die at 75° C. to produce a billet having a 10 mm diameter. A drill was used to create a hole, approximately 4 mm in diameter, into the drawn billet.

For the purposes of this disclosure, both of the drawn billets represent the sleeves of shape memory polymer material described above. Samples of both drawn billets were then immersed in hot water (80° C.) for 10 minutes to relax or deform the billets. The samples were then removed and allowed to cool to room temperature for 5 minutes. The relaxed billets were found to have the dimensions shown in Table 1.

TABLE 1

|         | Drawn        | Relaxed      |
|---------|--------------|--------------|
|         | First Billet |              |
| OD (mm) | 12.1 ± 0.1   | 18.6 ± 0.1   |
| ID (mm) | 5.9 ± 0.1    | 5.8 ± 0.1    |
|         | Second Billet |             |
| OD (mm) | 9.6 ± 0.1    | 17.5 ± 0.1   |
| ID (mm) | 4.4 ± 0.1    | 6.1 ± 0.1    |

Figure 3A:
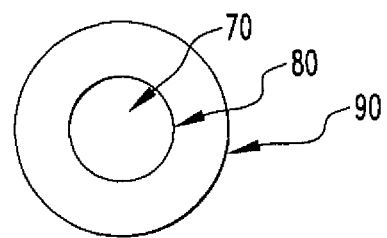
FIGS. 3A-3C show frontal views of polymer sleeves of the present disclosure before and after deformation of the sleeves.
Figure 3B:
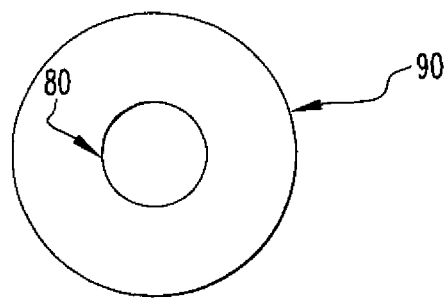

As shown in Table 1, the outer diameter of both billets and the inner diameter of the second billet increased significantly when the billets were provided with energy. However, the inner diameter of the first billet did not change upon providing the first billet with energy. FIGS. 3A-3B helps to explain this result. FIG. 3A shows a front view of a billet representing either the first or the second billet described above. The billet shows three different regions. Region 70 is the billet hole, region 80 is the inner diameter, and region 90 is the outer diameter. It is believed that drawing the first billet in the presence of the steel rod resulted in an uneven radial stress pattern between regions 80 and 90. Specifically, it is believed that the radial stress stored in region 80 of the billet located adjacent to the rod (the area of the inner diameter) was very low, the radial stress stored in region 90 of the billet located adjacent to the die interface was higher compared to region 90, and the material located between regions 80,90 had a varying level of stored radial stress depending on their proximity to regions 80,90. Therefore, the polymer in region 80, unlike the polymer in region 90, did not contain the shape memory qualities (stored stress) required for the inner diameter to change shape or expand radially upon providing the billet with energy, as shown in FIG. 3B. Since the inner diameter of the billet did not increase upon providing the billet with energy, it is believed that this type of billet would substantially reduce the above problems when the billet is used in connection with a medical device, namely inefficient heating of the billet and insufficient fixation of the device to bone.

In addition to the radial stress referred to above, stored stress would also be present along the length of the billet. This type of stress is referred to as axial stress. Therefore, each of regions 80,90 and the regions therebetween can be referred to as two-dimensional regions having one direction (radial) and another direction (axial) that are perpendicular to one another. Due to the billet shrinking axially upon providing the billet with energy, it is believed that the stored axial stress in regions 80,90 and therebetween is higher than at least the radial stress stored in region 80 of the billet. For the purposes of this disclosure, the axial stress in region 80 is higher than 0 and the radial stress in region 80 is about 0.

EXAMPLE TWO

Figure 1A:
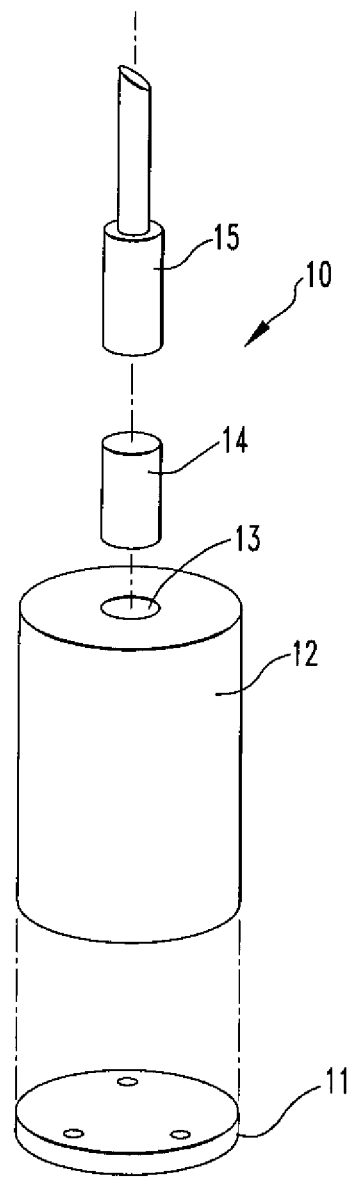
FIG. 1A shows a perspective view of a first embodiment of a compression mold set.

A composite material of PLLA-co-DL and 35% calcium carbonate (CaCO₃) was pre-dried overnight at a temperature of 50° C. using a Motan model Luxor CA15 hot air desiccant dryer. A compression mold set 10, shown in FIG. 1A, was used to compress the dried material. The mold set 10 includes a base plate 11 coupled to a mold body 12 having a through hole 13. Located within the through hole 13 of the mold body 12 is a spigot shaping insert 14. A plunger 15 is used to compact the material, as will be further described below. The through hole 13 is about 30 mm in diameter and the mold body has a length of about 300 mm and an outer diameter of about 75 mm. Although not shown, the spigot shaping insert 14 has a lead in diameter of 29.5 mm and continues to a final diameter of the intended drawn product. The insert 14 is 25 mm in length.

Prior to use, two 750 W heater bands were placed on the mold body 12 and the mold body 12 was heated to 165° C. for 20 minutes. The dried polymer composite material was then placed into the through hole of the heated mold body 12. The material was compacted by inserting the plunger 15 into the through hole 13 and applying a light load (<1000 N) on the plunger 15 via the use of an instron machine. This routine was repeated until the through hole 13 was completely filled with material. The material was compressed by applying a load of 3.5 kN to the plunger 15 via the use of a computer controlled Messphysik model Beta 20-10/8×15 testing machine. The heater bands were turned off and the mold 10 was allowed to cool while under a constant load of 3.5 kN. The load was released when the temperature of the mold 10 reached 50° C. The unloaded mold 10 was left to cool overnight. After cooling, the mold 10 was removed from the mechanical test machine and the base plate 11 was removed. The mold 10 was then was then transferred to a hydraulic press, which was used to push the spigot insert 14 and a molded billet out of the mold body 12.

Figure 2A:
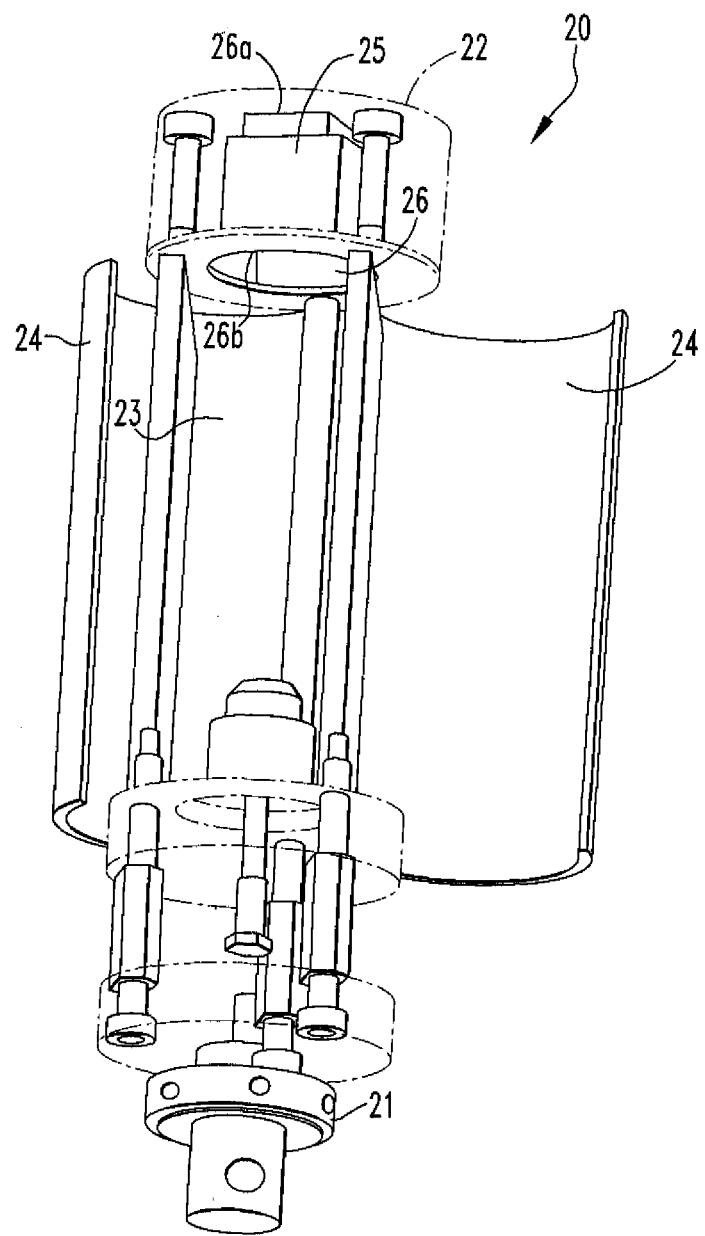
FIG. 2A shows a perspective view of a first embodiment of a die drawing rig.

The billet was then die drawn using a drawing rig 20 shown in FIG. 2A. The rig 20 includes a base portion 21, a die retainer 22, and a chamber 23. The chamber 23 includes chamber doors 24 that are closed during the die drawing process. A drawing die 25, including a through hole 26 having a diameter of 30 mm at the entrance 26a to the through hole 26 and a diameter of 15 mm at the exit 26b from the through hole 26, is located in the die retainer 22.

The base portion 21 was coupled to the platform of a computer Messphysik model Beta 20-10/8×15 testing machine using the location post. A 650 W heater band was clamped to the outside of the die retainer 22 of the rig 20. The billet was loaded into the rig 20 so that the spigot shaping insert 14 extended from the die 25. A clamp was attached to the cross head of the testing machine and subsequently coupled to the spigot 14 to prepare the spigot 14 for drawing. A hot air gun, (Steinel type 3483), with a set temperature of 70° C. was attached to the chamber doors 24 via a cowling (not shown). The drawing process was commenced when the die retainer had maintained a temperature of 75° C. for 20 minutes. The crosshead speed was set at 10 mm/min for the first 40 mm of drawing and then increased to 30 mm/min for the rest of the drawing process. The die drawn billet (15 mm diameter) was collected and a small 25 mm long plug was cut from the billet. A through hole (8 mm) was then drilled through the centre of the billet.

Figure 1B:
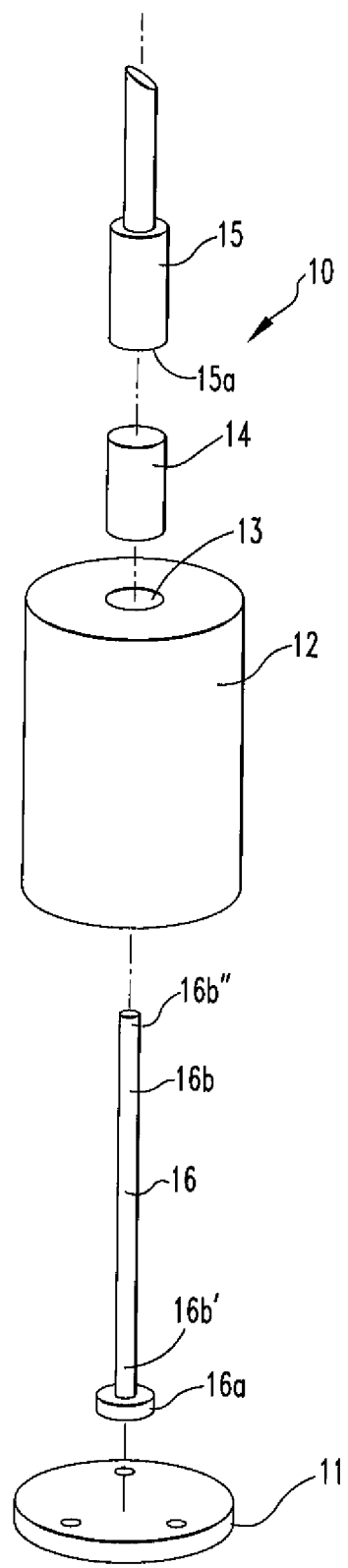
FIG. 1B shows a perspective view of a second embodiment of a compression mold set.

A second billet was made via a very similar process to the first billet. However, as shown in FIG. 1B, the mold 10 was assembled with a mandrel pin 16. The pin 16 includes a base 16a having a similar diameter to that of the through hole 13 and a shaft 16b having a first end 16b' coupled to the base 16a and a second end 16b". The pin 16 is located in the through hole 13 such that the second end 16b" of the pin 16 extends out of the mold body 12. Prior to use, the spigot shaping insert 14 was placed within the through hole 13 such that it was disposed on the shaft 16b of the pin 16. The plunger 15 included a hole 15a that was configured to fit over the shaft 16 during compaction and compression of the material. After compaction and compression of the material, as described above, the pin 16 and billet were extracted from the mold body 12 and the pin 16 was subsequently removed from the billet. A billet was produced having a 6 mm central through hole.

Figure 2B:
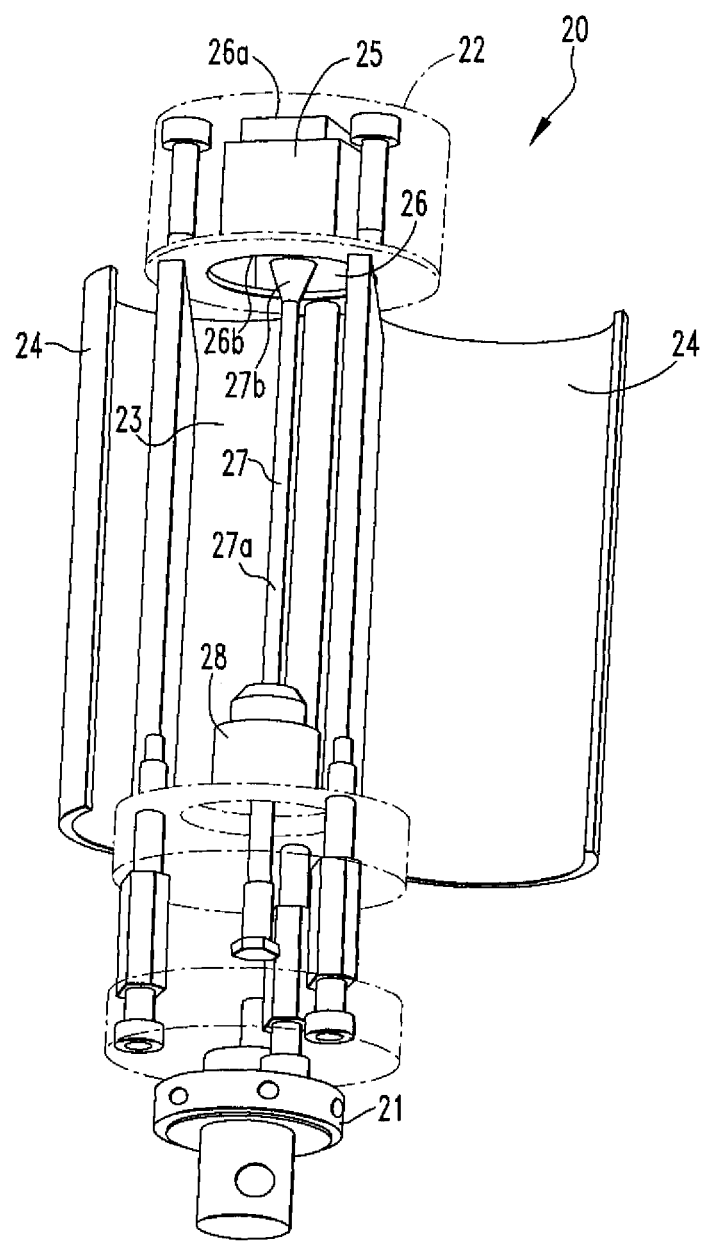
FIG. 2B shows a perspective view of a second embodiment of a die drawing rig.

The second billet was then die drawn using a drawing rig 20 shown in FIG. 2B. The rig 20 includes a base portion 21, a die retainer 22, and a chamber 23. The chamber 23 includes chamber doors 24 that are closed during the die drawing process and a chuck 28 for holding a mandrel, as will be described later. A drawing die 25, including a through hole 26 having a diameter of 30 mm at the entrance 26a to the through hole 26 and a diameter of 15 mm at the exit 26b from the through hole 26, is located in the die retainer 22.

The base portion 21 was coupled to the platform of a computer Messphysik model Beta 20-10/8×15 testing machine using the location post. A 650 W heater band was clamped to the outside of the die retainer 22 of the rig 20. The billet was loaded into the rig 20 so that the spigot shaping insert 14 extended from the die 25. A mandrel 27 was inserted into the billet prior to placing the billet in the rig 20. The mandrel 27 includes a first portion 27a that was held in place via use of the chuck 28 and a second portion 27b having a wider diameter (8 mm) and a transition from the wider diameter to the diameter of the first portion 27a through a 30° taper. The mandrel 27 was positioned such that the second portion 27b laid approximately level with the through hole exit 26b or about 1 mm short of it. A clamp was attached to the cross head of the testing machine and subsequently coupled to the spigot 14 to prepare the spigot 14 for drawing. A hot air gun, (Steinel type 3483), with a set temperature of 70° C. was attached to the chamber doors 24 via a cowling (not shown). The drawing process was commenced when the die retainer had maintained a temperature of 75° C. for 20 minutes. The crosshead speed was set at 10 mm/min for the first 40 mm of drawing and then increased to 30 min/min for the rest of the drawing process. The die drawn billet (15 mm diameter) was collected and a small 25 mm long plug was cut from the billet. The drawn billet had an 8 mm central through hole.

Figure 3C:
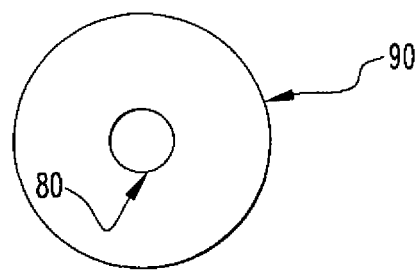

For the purposes of this disclosure, both of the drawn billets represent the sleeves of shape memory polymer material described above. Samples of the billet that was drawn without the use of a mandrel (Sample A) and of the billet that was drawn with the use of a mandrel (Sample B) were each placed in hot water (95° C.) for 10 minutes. The outer diameters of samples A and B and the outer diameter of sample A expanded to diameters of 27 mm, 27 mm, and 14 mm, respectively. However, the inner diameter of Sample B decreased to 5.7 mm. FIGS. 3A and 3C help to explain this. FIG. 3A shows a front view of a billet representing either the Sample A billet or the Sample B billet described above. The billet shows three different regions. Region 70 is the billet hole, region 80 is the inner diameter, and region 90 is the outer diameter. It is believed that when Sample B billet was drawn in the presence of the mandrel, opposite radial stress patterns between region 80 and region 90 resulted. Specifically, it is believed that the radial stress stored in region 80 of the billet adjacent to the mandrel was in opposite direction to the stored radial stress generated in region 90 located adjacent to the die interface. Therefore, upon providing energy to the billet, the billet expands radially such that region 90, corresponding to the outer diameter, increases and region 80, corresponding to the inner diameter, contracts or decreases radially, as shown in FIG. 3C. Since the radial stress stored in regions 80,90 are opposite to one another, it is believed that there is zero, or a very small amount of radial stored stress, located between regions 80,90.

In addition to the radial stress referred to above, stored stress would also be present along the length of the billet. This type of stress is referred to as axial stress. Therefore, each of regions 80,90 and the regions therebetween can be referred to as two-dimensional regions having one direction (radial) and another direction (axial) that are perpendicular to one another. Due to the billet shrinking axially upon providing the billet with energy, it is believed that the stored axial stress in regions 80,90 and therebetween is higher than at least the radial stress stored in region 80 of the billet. For the purposes of this disclosure, the axial stress in region 80 is higher than 0 and the radial stress in region 80 is about 0.

Drawing a billet through a mandrel, similar to the mandrel described above, but with a die having the same diameter as the outer surface of the billet is also within the scope of this disclosure. In this case, a radial stored stress would be present region 80 and no or a smaller amount of stress compared to region 80, would be present in region 90. Axial stored stress would still be present in regions 80,90. However, it is believed that the axial stored stress in region 90 would be higher than at least the radial stored stress in region 90 of the billet. For the purposes of this embodiment, the axial stress in region 90 is higher than 0 and the radial stress is about 0.

Figure 4A:
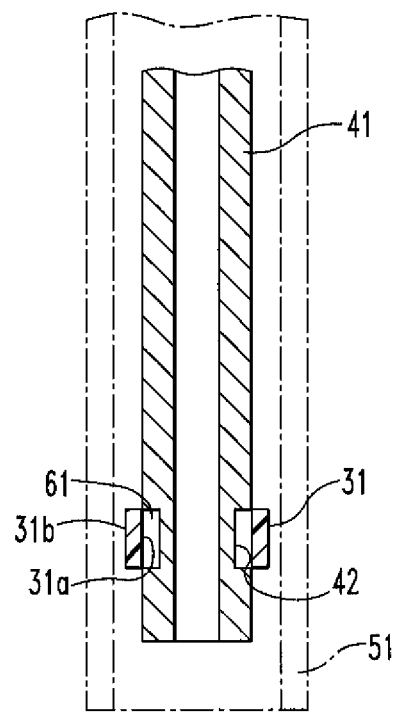
FIGS. 4A-4B show cross-sectional views of a medical device including a polymer sleeve of the present disclosure both before and after deformation of the sleeve.
Figure 4B:
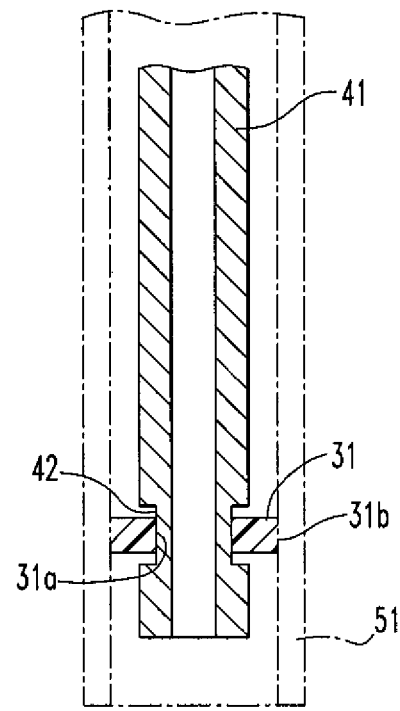

Since the inner diameter of the billet decreased radially upon providing the billet with energy, it is believed that this type of billet would substantially reduce the above problems when the billet is used in connection with a medical device, namely inefficient heating of the billet and insufficient fixation of the device to bone. This benefit is shown in FIGS. 4A and 4B. A sleeve of shape memory polymer material 31, such as the sleeve 31 described above for Sample B, is coupled to an interface portion 42 of an internal fixation device 41, such as an intramedullary nail, and the internal fixation device 41 is inserted into bone 51. The sleeve 31 is then provided with energy to deform the sleeve 31. A decrease in the inner diameter 31*a* of the sleeve 31 causes the sleeve 31 to grip the device 41 and an increase in the outer diameter 31*b* causes the outer diameter 31*b* to contact the bone 51, thereby filling the gap 61 between the bone 51 and the fixation device 41. As can be seen in FIG. 4B, axial shrinkage of the sleeve 31 also occurs.

The interface portion 42 of the fixation device 41 is the portion of the device 41 that the sleeve 31 is coupled to or interfaces with. This portion may be located anywhere along the length of the device 41 and may be of a lesser diameter than the rest of the device 41 or the same diameter as the rest of the device 41. A surface of the interface portion 42 may include texture, such as grooves, engravings, or other types of texture that would allow further engagement of the sleeve 31 to the device 41. In addition, the interface portion 42 may be machined to have any shape. The shapes and surfaces may be machined, molded, cast, laser cut, or chemically etched into the internal fixation device 41 or formed via another method known to one of ordinary skill in the art.

Instead of using the sleeve of shape memory polymer material described above for Sample B, the sleeve described above for the first billet may also be used. In this case, as described above, once the sleeve is provided with energy, the outer diameter would increase to engage the bone and the inner diameter would remain unchanged. Hence, the sleeve would fixate the device to the bone and coupling of the sleeve to the device would remain unchanged.

The sleeves described above and shown in the figures are cylindrical. However, the sleeves may be other shapes including, without limitation, rectangular or square.

For the purposes of this disclosure, the polymer includes PDLAGA and PLLA-co-DL. However, any biocompatible, shape memory polymeric material may be used, including, an amorphous polymer, a semi-crystalline polymer, and combinations thereof. Specific polymer may include, without limitation, poly-alpha-hydroxy acids, polycaprolactones, polydioxanones, polyesters, polyglycolic acid, polyglycols, polylactides, polyorthoesters, polyphosphates, polyoxaesters, polyphosphoesters, polyphosphonates, polysaccharides, polytyrosine carbonates, polyurethanes, polyacrylic/polyacrylates, polymethyl methacrylate, polybutyl methacrylate, polybutyl methacrylate-co-polymethyl methacrylate, polyethyl methacrylate, polybutylacrylate, polystyrene, polyolefin, polyethylene, poly-alpha-hydroxy acids, and copolymers or polymer blends thereof. Polyesters that may be used include P(L)LA, poly (D) lactic acid (P(D)LA), poly (DL) lactic acid (P(DL)LA), poly(L-co-DL) lactic acid (P(LDL)LA), poly (L) lactic acid-co-glycolide (P(L)LGA)), poly (DL) lactic acid-co-glycolide (P(DL)LGA)), poly (D) lactic acid-co-glycolide (P(D)LGA)), polycaprolactone (PCL), PGA, and combinations thereof. In addition, the polymer may be resorbable or non-resorbable.

Also for the purposes of this disclosure, the composite includes calcium carbonate as a filler material. However, other filler materials may also be used, including, without limitation, tricalcium phosphate (TCP), calcium sulphate, carbon nanotubes, degradable ceramic, and degradable glass. In addition, the rod used in connection with the billet during the die drawing process, as described above, is a stainless steel rod. However, the rod may be of another material, including, without limitation, plastic, ceramic, or combinations thereof. The rod may also have a range of cross-sectional profiles, including, without limitation, round, square, star-shaped, and triangular. In addition, the rod may have a consistent cross-sectional area or a varying cross-sectional area and the surface of the rod may be smooth or have a pattern to allow the drawn polymer billet to integrate with the surface.

Examples of adding energy to the polymer material include electrical and thermal energy sources, the use of force, or mechanical energy, and/or a solvent. Any suitable force that can be applied either preoperatively or intra-operatively can be used. One example includes the use of ultra sonic devices, which can relax the polymer material with minimal heat generation. Solvents that could be used include organic-based solvents and aqueous-based solvents, including body fluids. Care should be taken that the selected solvent is not contra indicated for the patient, particularly when the solvent is used intra-operatively. The choice of solvents will also be selected based upon the material to be relaxed. Examples of solvents that can be used to relax the polymer material include alcohols, glycols, glycol ethers, oils, fatty acids, acetates, acetylenes, ketones, aromatic hydrocarbon solvents, and chlorinated solvents.

The polymeric material may include a composite or matrix having reinforcing material or phases such as glass fibers, carbon fibers, polymeric fibers, ceramic fibers, ceramic particulates, rods, platelets, and fillers. Other reinforcing material or phases known to one of ordinary skill in the art may also be used. In addition, the polymeric material may be made to porous via the use of porogens. The porogens include sodium chloride, lithium bromide, lithium iodide, calcium chloride, sodium iodide, magnesium sulphate, and calcium sulphate. Porosity may allow infiltration by cells from surrounding tissues, thereby enhancing the integration of the material to the tissue. Also, one or more active agents may be incorporated into the material. Suitable active agents include bone morphogenic proteins, antibiotics, anti-inflammatories, angiogenic factors, osteogenic factors, monobutyrin, thrombin, modified proteins, platelet rich plasma/solution, platelet poor plasma/solution, bone marrow aspirate, and any cells sourced from flora or fauna, such as living cells, preserved cells, dormant cells, and dead cells. It will be appreciated that other bioactive agents known to one of ordinary skill in the art may also be used. Preferably, the active agent is incorporated into the polymeric shape memory material, to be released during the relaxation or degradation of the polymer material. Advantageously, the incorporation of an active agent can act to combat infection at the site of implantation and/or to promote new tissue growth.

For the purposes of this disclosure, the sleeves are used in medical applications. However, sleeves for use in non-medical applications are also within the scope of this disclosure.

In view of the foregoing, it will be seen that the several advantages of the disclosure are achieved and attained.

The embodiments were chosen and described in order to best explain the principles of the disclosure and its practical application to thereby enable others skilled in the art to best utilize the disclosure in various embodiments and with various modifications as are suited to the particular use contemplated.

As various modifications could be made in the constructions and methods herein described and illustrated without departing from the scope of the disclosure, it is intended that all matter contained in the foregoing description or shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A sleeve of shape memory polymer material having an inner surface region and an outer surface region, wherein the sleeve includes a stored radial stress located on the inner surface region of the sleeve and a stored radial stress located on the outer surface region of the sleeve, the stored radial stress on the outer surface region being higher than the stored radial stress on the inner surface region.

2. The sleeve of shape memory polymer material of claim 1 wherein the sleeve has the shape of a cannulated cylinder.

3. The sleeve of shape memory polymer material of claim 2 in which the inner surface region comprises an inner surface of the cylinder.

4. The sleeve of shape memory polymer material of claim 2 in which the outer surface region comprises an outer surface of the cylinder.

5. The sleeve of shape memory polymer material of claim 1 wherein the sleeve has the shape of a cannulated rectangle or square.

6. The sleeve of shape memory polymer material of claim 1 wherein the sleeve has a tailored stress pattern wherein the outer surface region of the sleeve expands in a radial direction and the inner surface region of the sleeve contracts in a radial direction simultaneously upon providing energy to the sleeve.

7. The sleeve of shape memory polymer material of claim 1 wherein the polymer material is resorbable.

8. The sleeve of shape memory polymer material of claim 1 wherein the polymer material is non-resorbable.

9. The sleeve of shape memory polymer material of claim 1 wherein the material includes a filler selected from a group consisting essentially of hydroxyapatite, calcium carbonate, and tricalcium phosphate.

10. The sleeve of shape memory polymer material of claim 1 wherein the material includes a porogen selected from a group consisting essentially of sodium chloride, lithium bromide, lithium iodide, calcium chloride, sodium iodide, magnesium sulphate, and calcium sulphate.

11. The sleeve of shape memory polymer material of claim 1 wherein the polymer material includes a polyester selected from a group including P(L)LA, poly (D) lactic acid (P(D) LA), poly (DL) lactic acid (P(DL)LA), poly(L-co-DL) lactic acid (P(LDL)LA), poly (L) lactic acid-co-glycolide (P(L) LGA)), poly (DL) lactic acid-co-glycolide (P(DL)LGA)), poly (D) lactic acid-co-glycolide (P(D)LGA)), polycaprolactone (PCL), PGA, and combinations thereof.

12. The sleeve of shape memory polymer material of claim 1 wherein the material includes a polyacrylate.

13. The sleeve of shape memory polymer material of claim 1 wherein the material includes a polymethyl methacrylate polymer or copolymer thereof.

14. The sleeve of shape memory polymer material of claim 1 wherein the material includes a polybutyl methacrylate polymer or copolymer thereof.

15. The sleeve of shape memory polymer material of claim 1 wherein the material includes a polybutyl methacrylate-co-polymethyl methacrylate copolymer.

16. The sleeve of shape memory polymer material of claim 1 wherein the material includes a polystyrene copolymer.

* * * * *